(12) United States Patent
Portela et al.

(10) Patent No.: US 11,672,948 B2
(45) Date of Patent: *Jun. 13, 2023

(54) URINARY CATHETER, KIT AND METHOD (71) Applicant: Portela Soni Medical, Inc., Attleboro, MA (US)

(72) Inventors: Francisco Portela, Attleboro, MA (US); Amit Soni, North Aurora, IL (US); Juan Ramon Portela, Attleboro, MA (US)

(73) Assignee: Portela Soni Medical, Inc., Attleboro, MA (US)

( * ) Notice: Subject to any disclaimer, the term of this patent is extended or adjusted under 35 U.S.C. 154(b) by 431 days.

This patent is subject to a terminal disclaimer.

(21) Appl. No.: 16/859,063

(22) Filed: Apr. 27, 2020

(65) Prior Publication Data

US 2020/0254215 A1    Aug. 13, 2020

Related U.S. Application Data

(63) Continuation of application No. 15/019,540, filed on Feb. 9, 2016, now Pat. No. 10,668,246.
(Continued)

(51) Int. Cl.
*A61M 25/00* (2006.01)
*A61M 25/10* (2013.01)
(Continued)

(52) U.S. Cl.
CPC ...... *A61M 25/0026* (2013.01); *A61M 25/003* (2013.01); *A61M 25/0017* (2013.01);
(Continued)

(58) Field of Classification Search
CPC .......... A61M 25/0017; A61M 25/0068; A61M 2025/0073; A61M 2025/1093;
(Continued)

(56) References Cited

U.S. PATENT DOCUMENTS 2,547,758 A    4/1951  Keeling
3,630,206 A    12/1971 Gingold
(Continued)

FOREIGN PATENT DOCUMENTS

GB       2169206 A      7/1986
WO    1999/07420 A1     2/1999
(Continued)

OTHER PUBLICATIONS

European Office Action for Application No. 16752811.6, dated Feb. 14, 2022, 6 pages.
(Continued)

*Primary Examiner* — Adam Marcetich
(74) *Attorney, Agent, or Firm* — McCarter & English, LLP; Jonathan C. Lovely (57) ABSTRACT

The invention provides a catheter including: a first lumen adapted for draining a first fluid from a subject; a second lumen adapted for passing a second fluid through the second lumen; and a third lumen adapted for passing a third fluid through the third lumen such that the third fluid can exit the third lumen to bathe at least a part of an outside surface of the catheter. The invention further provides a kit and/or system including said catheter and method of use for said catheter.

18 Claims, 9 Drawing Sheets

Related U.S. Application Data (60) Provisional application No. 62/118,727, filed on Feb. 20, 2015.

(51) Int. Cl.
  *A61M 39/24* (2006.01)
  *A61M 27/00* (2006.01)

(52) U.S. Cl.
  CPC .............. *A61M 25/10* (2013.01); *A61M 27/00* (2013.01); *A61M 39/24* (2013.01); *A61M 2025/0019* (2013.01); *A61M 2025/0076* (2013.01); *A61M 2202/0496* (2013.01)

(58) Field of Classification Search
  CPC .............. A61M 25/007; A61M 3/0283; A61M 25/0067; A61M 3/0279; A61B 1/00091; A61B 1/126; A61B 1/128; A61B 1/12; A61B 1/00156; A61B 2217/007; B05B 1/26; B05B 1/262
  See application file for complete search history.

(56) References Cited

U.S. PATENT DOCUMENTS

| | | | |
|---|---|---|---|
| 3,828,767 A * | 8/1974 | Spiroff | A61M 25/0015 604/523 |
| 3,995,617 A | 12/1976 | Watkins et al. | |
| 4,211,233 A | 7/1980 | Lin | |
| RE30,365 E | 8/1980 | Mattler | |
| 4,501,580 A | 2/1985 | Glassman | |
| 4,579,554 A | 4/1986 | Glassman | |
| 4,723,946 A | 2/1988 | Kay | |
| 4,878,893 A * | 11/1989 | Chin | A61B 1/00085 604/105 |
| 5,147,334 A * | 9/1992 | Moss | A61M 25/007 604/264 |
| 5,250,029 A | 10/1993 | Lin et al. | |
| 5,300,022 A | 4/1994 | Klapper et al. | |
| 5,609,583 A | 3/1997 | Hakki et al. | |
| 5,688,239 A | 11/1997 | Walker | |
| 5,695,481 A * | 12/1997 | Heinzelman | A61M 3/0279 604/264 |
| 6,080,142 A | 6/2000 | Sachse | |
| 6,090,069 A | 7/2000 | Walker | |
| 6,293,958 B1 | 9/2001 | Berry et al. | |
| 6,299,598 B1 | 10/2001 | Bander | |
| 6,592,564 B2 | 7/2003 | Finch et al. | |
| 6,758,857 B2 | 7/2004 | Cioanta | |
| 7,381,190 B2 | 6/2008 | Sugrue et al. | |
| 7,776,005 B2 | 8/2010 | Haggstrom et al. | |
| 3,409,171 A1 | 4/2013 | Hannon et al. | |
| 2002/0016564 A1 | 2/2002 | Courtney et al. | |
| 2005/0006421 A1 | 1/2005 | Shu | |
| 2005/0267334 A1 | 12/2005 | Swain et al. | |
| 2005/0277803 A1 | 12/2005 | Pecor | |
| 2006/0142702 A1 * | 6/2006 | Sievers | A61M 25/007 604/264 |
| 2006/0229550 A1 * | 10/2006 | Staid | A61B 17/3203 604/27 |
| 2007/0255256 A1 | 11/2007 | Fischer et al. | |
| 2008/0172040 A1 | 7/2008 | Smith | |
| 2008/0262477 A1 | 10/2008 | Djaladat | |
| 2009/0054825 A1 | 2/2009 | Melsheimer et al. | |
| 2009/0101152 A1 | 4/2009 | Burk et al. | |
| 2009/0171241 A1 | 7/2009 | Garcia et al. | |
| 2009/0240197 A1 * | 9/2009 | Cowan | A61M 25/0116 604/528 |
| 2009/0240234 A1 | 9/2009 | Doerr | |
| 2011/0034865 A1 | 2/2011 | Wallace | |
| 2011/0152908 A1 | 6/2011 | Morris et al. | |
| 2011/0166547 A1 | 7/2011 | Baumbach et al. | |
| 2011/0172590 A1 | 7/2011 | Akahoshi | |
| 2011/0311602 A1 | 12/2011 | Mills et al. | |
| 2012/0150130 A1 | 6/2012 | Friel et al. | |
| 2012/0232503 A1 | 9/2012 | Macy, Jr. | |
| 2013/0085438 A1 * | 4/2013 | MacMeans | A61M 25/00 604/523 |
| 2013/0184683 A1 | 7/2013 | Chow et al. | |
| 2013/0267888 A1 | 10/2013 | Rhodes et al. | |
| 2014/0155830 A1 | 6/2014 | Bonnette et al. | |
| 2014/0221980 A1 * | 8/2014 | Rontal | A61M 3/0283 604/98.01 |
| 2016/0030713 A1 | 2/2016 | Galinat | |
| 2016/0067444 A1 | 3/2016 | Allen et al. | |
| 2016/0243332 A1 | 8/2016 | Portela et al. | |

FOREIGN PATENT DOCUMENTS

| | | |
|---|---|---|
| WO | 2011/008758 A2 | 1/2011 |
| WO | 2014/140093 A1 | 9/2014 |

OTHER PUBLICATIONS

Thomsen et al., Male urethral catheterization. N Engl J Med. May 25, 2006;354(21):e22. 3 pages.

International Search Report and Written Opinion for PCT/US2016/017134 filed Feb. 9, 2016, dated Apr. 19, 2016 and mailed May 20, 2016 by the ISA/US.

Supplementary European Search Report issued for EP Application 16752811 dated Oct. 12, 2018.

* cited by examiner

URINARY CATHETER, KIT AND METHOD

PRIORITY

This patent application is a continuation application of and claims priority from U.S. application Ser. No. 15/019,540, filed Feb. 9, 2016, entitled "Urinary Catheter, Kit and Method," and naming Francisco Portela, Amit Soni and Juan Ramon Portela as inventors, the disclosure of which is incorporated herein, in its entirety by reference.

U.S. application Ser. No. 15/019,540, in turn, claims priority to U.S. Provisional Application No. 62/118,727, filed Feb. 20, 2015, "Urinary Catheter, Kit and Method," and naming Francisco Portela and Amit Soni as inventors, the disclosure of which is incorporated herein, in its entirety by reference.

BACKGROUND OF THE INVENTION

The present invention provides innovative solutions to common problems associated with the use of a catheter, such as, for a non-limiting example, a urinary catheter, by providing a novel catheter, a novel kit and/or system including said catheter and a novel method employing the use of said catheter, kit and/or system. The present invention can replace the current standard practices when a catheter is indicated.

According to the Centers for Disease Control, 15-25% of all hospitalized patients will receive a urinary catheter during their stay. Urinary catheters are used in a variety of ways including, but not limited to, drainage of fluids related to the bladder, bladder wall punctures, bladder spasms, and urethral wall atony and/or atrophy. Problems associated with urinary catheter use include tissue trauma upon insertion, urinary tract infection, bladder spasm, bladder wall puncture, urethral erosion, genitourinary pain, and catheter obstruction. Catheters can also be attributed to complications such as prostatitis, epididymitis, and orchitis in males, and cystitis, pyelonephritis, gram-negative bacteremia, endocarditis, vertebral osteomyelitis, septic arthritis, endophthalmitis, and meningitis in all patients. Centers for Disease Control. (2015). *Urinary Tract Infection (Catheter-Associated Urinary Tract Infection [CAUTI] and Non-Catheter-Associated Urinary Tract Infection [UTI]) and Other Urinary System Infection [USI] Events* http://www.cdc.gov/nhsn/pdfs/pscManual/7pscCAUTIcurrent.pdf. Among all hospital-acquired infections, catheter-associated urinary tract infections ("CAUTI") compose 40% of all of these nosocomial infections. Hooton, T., Bradley, S., Cardenas, D., Colgan, R., Geerlings, S., Rice, J. (2009). *Diagnosis, Prevention, and Treatment of Catheter-Associated Urinary Tract Infection in Adults:* 2009 *International Clinical Practice Guidelines from the Infectious Diseases Society of America* http://cid.oxfordjournals.org/content/50/5/625.full.pdf+html. Current government and industry guidelines now recommend catheterizing patients with specific clinical indications and discontinuing use as quickly as possible due to chance of CAUTI being an accumulating 3-10% per day. Members of the Jury of Consensus Conference on nosocomial urinary tract infections (NUTI) in adult patients. (2003). *Nosocomial urinary tract infections (NUTI) in adult patients: Consensus conference* 2002, *short text* http://www.infectiologie.com/site/medias/english/noso-uti2002.pdf.

For many years, companies in the catheter industry have responded to the CAUTI with ineffective solutions which at times have compounded the CAUTI problem. For example, some companies have experimented with applying antimicrobial coatings to their catheters to prevent the formation of biofilms on the catheter surfaces which lead to infection. Studies have shown that antimicrobial-coated and silver-coated catheters have had little effect on infection rates and in some cases, have even lead to the creation of drug-resistant bacterial infection due to the nature of rapid bacterial division and adaptation. For high-risk patients, generally the elderly, a UTI can greatly increase the costs of the hospital stay and can result in subsequent complications and sometimes even death. Some physicians now recommend a suprapubic catheter (a catheter surgically placed from the abdominal wall into the bladder) for urinary drainage for high-risk patients due to the decreased chances of infection and subsequent complications. Another alternative to urethral catheterization includes external condom catheters in males for longer durations.

Thus, there is a need for the development of a novel catheter which will be less susceptible to the growth of biofilms on catheter surfaces thereby reducing the risk of CAUTIs and other infections.

BRIEF SUMMARY OF THE INVENTION

The invention features a novel improved catheter including: a first lumen for collecting a first fluid; an optional second lumen for passing a select amount of a second fluid, including for a non-limiting example, an inflation fluid, into a reversibly inflatable device; and a third lumen adapted for passing a third fluid including, for a non-limiting example, a flushing fluid, through the third lumen and bathing at least a portion of an outside surface of the catheter. The catheter can include an indwelling catheter or a catheter adapted for non-indwelling use.

In one aspect, the invention provides a catheter including a first lumen adapted for draining a first fluid from a subject; a second lumen adapted for passing a second fluid through the second lumen; and a third lumen adapted for passing a third fluid through the third lumen thereby bathing at least a part of an outside surface of the catheter.

In one embodiment, the first lumen includes at least one drainage eye disposed at a distal end of the first lumen and having a smooth outer edge.

In another embodiment, the catheter includes a lower portion having a lower portion diameter, a first end disposed contiguous with a proximal end of the catheter, a second end substantially opposed to the first end, and an intermediate area extending from an intermediate circumference of the lower portion to the second end of the lower portion; an upper portion having an upper portion diameter, a first end, and a second end substantially opposed to the first end and contiguous with a closed insertable tip of the catheter; and a bulb portion having a first bulb end having a first bulb end diameter, a second bulb end substantially opposed to the first bulb end and having a second bulb end diameter, the second bulb end being contiguous with the first end of the upper portion, the first bulb end diameter being greater that the lower portion diameter and the second bulb end diameter, the first end being disposed proximate to and surrounding the intermediate circumference of the lower portion, and at least part of an inner surface of the bulb portion forming an enclosure including a cavity surrounding an outer surface of the intermediate area of the lower portion.

In still another embodiment, the lower portion diameter and the first bulb end diameter are selected to form a predetermined gap between at least a part of an outer surface of the catheter and a wall of a passage of the subject upon insertion of the catheter into the subject.

In yet another embodiment, the bulb portion is disposed at a predetermined distance from the closed insertable tip of the catheter to minimize disruption of a tissue of the subject upon insertion of the catheter into the subject.

In another embodiment, the catheter includes a substantially straight lower portion and a substantially straight upper portion.

In a further embodiment, the second lumen includes an attachment port disposed proximate to a distal end of the second lumen and configured for attachment to a reversibly inflatable device.

In still a further embodiment, the catheter includes the reversibly inflatable device attached to the attachment port.

In another embodiment, the catheter includes a substantially straight tube having at least one of a non-varying diameter and a varying diameter.

In yet another embodiment, the third lumen includes a primary lumen having a first end contiguous with a proximal end of the catheter and a second end substantially opposed to the first end. The third lumen also includes at least one branch lumen having a first end contiguous with the second end of the primary lumen and having a second end substantially opposed to the first end of the branch lumen. In a preferred embodiment, the third lumen also includes at least two branch lumens each having a first end contiguous with the second end of the primary lumen and each branch lumen having a second end substantially opposed to the first end of the respective branch lumen, each branch lumen in fluidic communication with the primary lumen, and each branch lumen branching out in a direction substantially opposed to the other branch lumen.

In still another embodiment, at least one of the first, the second and the third lumens has a circular cross-section.

In a further embodiment, the outer surface of the catheter is selected from the group consisting of a smooth outer surface and a grooved outer surface.

In yet a further embodiment, at least two of the first fluid, the second fluid, and the third fluid have a substantially same composition.

In another embodiment, the catheter includes a kit including a device adapted for or at least one of injection into and withdrawal from the catheter of at least one of the first fluid, the second fluid, and the third fluid.

The invention also features in another aspect a method of drawing a first fluid from a subject. The method includes providing a catheter including: a first lumen adapted for passing a first fluid through the first lumen, a second lumen adapted for passing a second fluid through the second lumen, and a third lumen adapted for passing a third fluid through the third lumen. This aspect of the invention also includes inserting a closed insertable tip of the catheter into a passage of the subject; injecting the second fluid into a proximal end of the second lumen, and passing the second fluid through and out of the second lumen at a distal end substantially opposed to the proximal end of the second lumen into a reversibly inflatable device thereby inflating the device; injecting the third fluid into the third lumen at a proximal end of the third lumen, and passing the third fluid through and out of the third lumen at a distal end substantially opposed to the proximal end of the third lumen thereby bathing at least a part of an outside surface of the catheter; and draining through the first lumen the first fluid from the subject.

In an embodiment of this aspect, the method of the invention features providing the catheter including the first lumen comprising at least one drainage eye disposed at a distal end of the first lumen and having a smooth outer edge.

In another embodiment, the method of the invention includes providing the catheter including a lower portion having a lower portion diameter, a first end contiguous with a proximal end of the catheter, a second end substantially opposed to the first end, and an intermediate area extending from an intermediate circumference of the lower portion to the second end of the lower portion; an upper portion having an upper portion diameter, a first end, and a second end substantially opposed to the first end and contiguous with a closed insertable tip of the catheter; and a bulb portion having a first bulb end having a first bulb end diameter, a second bulb end substantially opposed to the first bulb end and having a second bulb end diameter, the second bulb end being contiguous with the first end of the upper portion, the first bulb end diameter being greater that the lower portion diameter and the second bulb end diameter, the first bulb end being disposed proximate to and surrounding the intermediate circumference of the lower portion, and at least part of an inner surface of the bulb portion forming an enclosure including a cavity surrounding an outer surface of the intermediate area of the lower portion.

In a further embodiment, the providing step of the method of the invention includes selecting the lower portion diameter and the first bulb end diameter to form a predetermined gap between at least a part of an outer surface of the catheter and a wall of a passage of the subject upon insertion of the catheter into the subject.

In still a further embodiment, the providing step of the method of the invention includes providing the catheter having the bulb portion disposed at a predetermined distance from the closed insertable tip of the catheter to avoid stimulation of a tissue of the subject upon insertion of the catheter into the subject.

In another embodiment, the providing step of the method of the invention includes providing the catheter including a substantially straight lower portion and a substantially straight upper portion.

In a further embodiment, the providing step of the method of the invention includes providing the catheter including the second lumen including an attachment port disposed proximate to a distal end of the second lumen and configured for attachment to the reversibly inflatable device.

In still a further embodiment, the providing step of the method of the invention includes providing the catheter including the reversibly inflatable device attached to the attachment port.

In another embodiment, the providing step of the method of the invention includes providing the catheter including a substantially straight tube having at least one of a non-varying diameter and a varying diameter.

In another embodiment, the providing step of the method of the invention includes providing the catheter including a primary lumen having a first end contiguous with a proximal end of the catheter and a second end substantially opposed to the first end, and at least one branch lumen having a first end contiguous with the second end of the primary lumen and having a second end substantially opposed to the first end of the branch lumen. In a preferred embodiment, the providing step of the method of the invention includes providing the catheter including the third lumen including at least two branch lumens each having a first end contiguous with the second end of the primary lumen and each having a second end substantially opposed to the first end, each branch lumen in fluidic communication with the primary lumen and branching out in a direction substantially opposed to the other branch lumen.

In still another embodiment, the providing step of the method of the invention includes providing the catheter having at least one of the first, the second and the third lumens including a circular cross-section.

In yet another embodiment, the providing step of the method of the invention includes providing the catheter having the outer surface of the catheter selected from the group consisting of a smooth outer surface and a grooved outer surface.

In a further embodiment, the method of the invention includes withdrawing the second fluid from the reversibly inflatable device thereby deflating the reversibly inflatable device; and removing the catheter from the subject.

BRIEF DESCRIPTION OF THE SEVERAL VIEWS OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION OF THE INVENTION

The present invention provides a novel catheter adapted to be placed within a passage of a subject such as, for a non-limiting example a urethra. The novel catheter is adapted to be capable of expelling fluid inside the passage in order to flush the space between the membrane and the catheter surface with a solution including, for example, a water, a saline, a urine-like solution or another flushing fluid known to those of ordinary skill in the art. This process mimics normal bodily functions which keep infections, such as for a non-limiting example, urinary tract infections, at bay by expelling bacteria from the passage and restoring a non-conducive environment for bacterial growth and colonization. The novel catheter is made from materials known to those of ordinary skill in the art which demonstrate low bacterial adherence surface and increased insertion comfort for the patient. In a preferable embodiment, the novel catheter of the invention consists of 100% silicone or silicone-coated latex. The novel improved catheter can be adapted for use as an indwelling catheter or as a substantially straight catheter for non-indwelling use.

Figure 1:
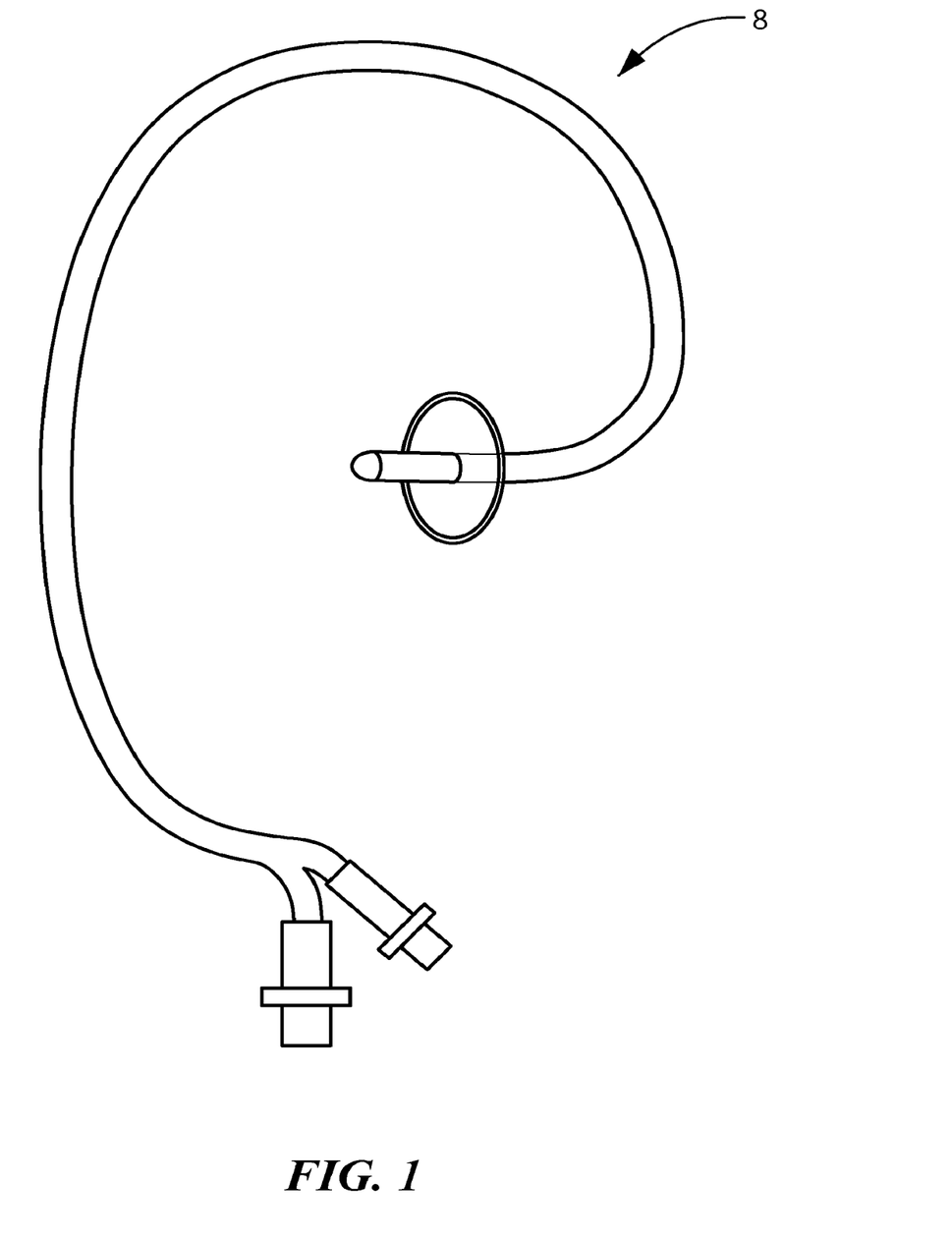
FIG. 1 illustrates prior art and background of the invention; 2A is a sectional view according to one embodiment of the present invention.

In order to better appreciate the novel improvements of the present invention, a traditional standard indwelling catheter such as the Foley catheter (8), is shown in FIG. 1 for comparison. http://doctorsgate.blogspot.com/2010/11/foley-catheter.html. The design of this catheter has not changed significantly for over 50 years. The Foley catheter is a flexible, resilient tube that is often passed through the urethra and into the bladder. The tube has a closed insertable distal tip for insertion into a subject and an open end for the passage of entering and exiting fluids. The tube typically has two separated channels, or lumens, running down its length. Urine drains from the bladder into the first lumen at its distal end, and travels through the first lumen into a collection bag disposed at the proximal end of the first lumen. The second lumen of the indwelling catheter is adapted for balloon inflation wherein a balloon disposed at a distal end of the second lumen. An inflating fluid is injected into the proximal end of the second lumen. The inflation fluid travels the length of the second lumen and inflates the balloon at the distal end. Once inflated, the expanded balloon allows the catheter to remain fixed in the bladder. In comparison to non-indwelling catheters such as intermittent or short term catheters, Foley indwelling catheters are used for longer terms of insertion.

Biofilms are prone to develop on the surfaces of the Foley catheter after the catheter is inserted within a subject. The biofilms are formed by bacteria which attach to the catheter surfaces. The bacteria can be slow dividing and develop with thick walls which are resistant to many antibiotics. The bacteria are internally "programmed" to detach from current growths. Detached bacteria can migrate causing widespread infection and obstruction. For example, after formation on a Foley catheter surface, bacteria can migrate to the bladder within one to three days. The bacteria can create crystalline formations and cause encrustations and blockages.

Figure 2A:
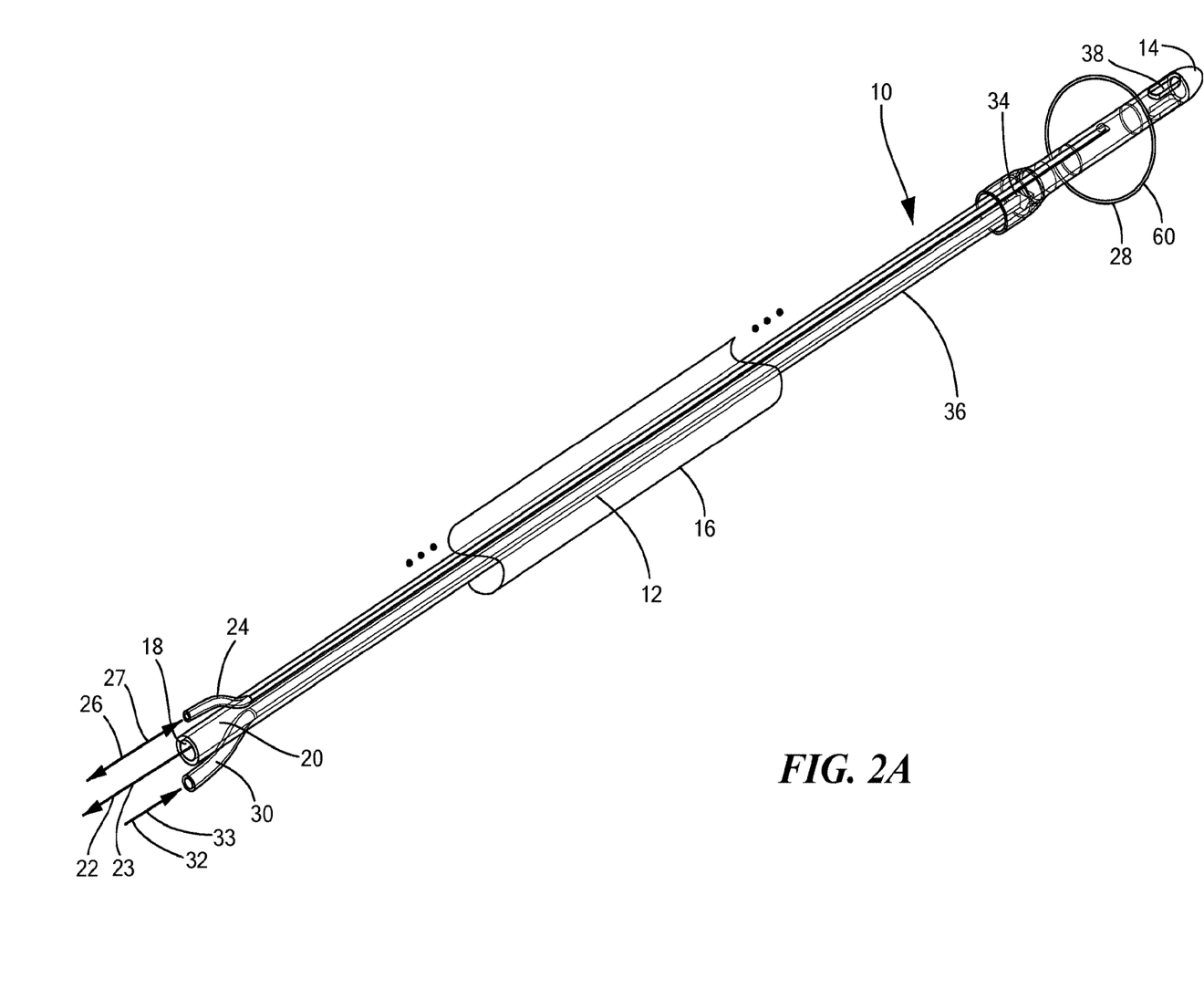

The novel improved catheter (10) of the present invention also includes a flexible, resilient tube (12) with a closed insertable distal tip (14) adapted for insertion into a subject, and in particular, a passage (16) or canal of the subject, and an open proximal end (18) adapted for the passage of fluids entering and exiting the catheter, as shown in FIG. 2A. In contrast to the traditional indwelling catheter which typically includes two lumens, in one aspect, the novel improved catheter of the invention includes three lumens. The first lumen (20) is adapted for drainage of the first fluid (22) from the subject. In a preferred embodiment, the first fluid (22) includes urine (23) and the first lumen (20) is adapted for drainage of urine (23) through the urethra from the bladder of the subject. In other embodiments, the first fluid (22) can include blood, pus, mucus, and/or other fluids, and the first lumen is thus adapted for drainage of such fluids. The second lumen (24) is adapted for passage of a select amount of a second fluid (26) through the second lumen (24). In a preferred embodiment, the second fluid (26) is an inflation fluid (27) and the second lumen (24) is adapted to pass the inflation fluid (27) through the second lumen (24) into a reversibly inflatable device (28), such as, for a non-limiting example, a catheter balloon (60). The third lumen (30) is adapted for passing a select amount of a third fluid (32) through the third lumen (30). In a preferred embodiment, the third fluid (32) includes a flushing fluid (33) and the third lumen (30) is adapted for passing the flushing fluid (33) through the third lumen (30) such that the flushing fluid exits the third lumen (30) at a distal end (34) of the third lumen (30) and bathes at least a part of the outside surface (36) of the tube (12) of the catheter (10).

Figure 2B:
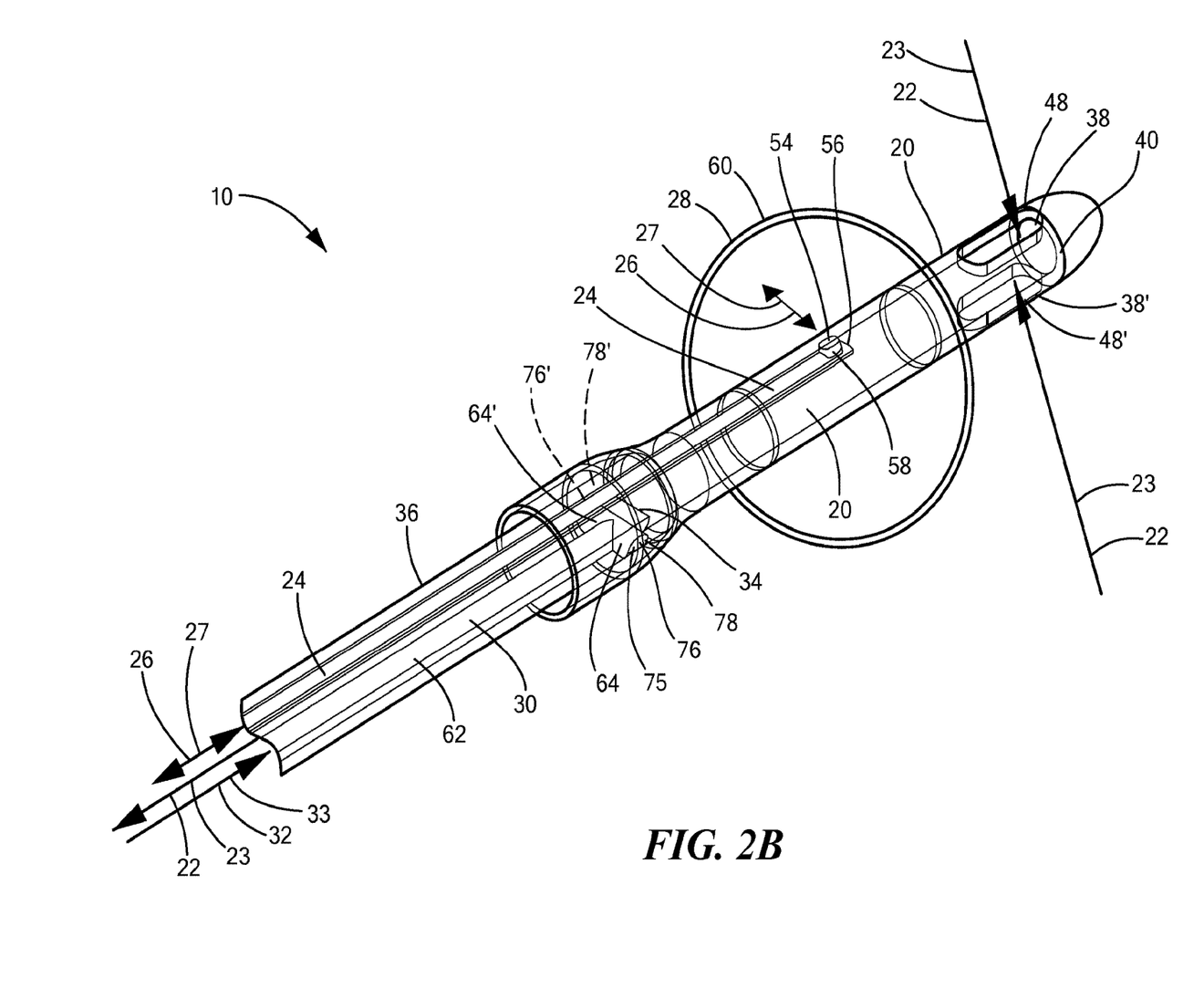
FIG. 2B is a sectional view according to one embodiment of the invention.
Figure 2C:
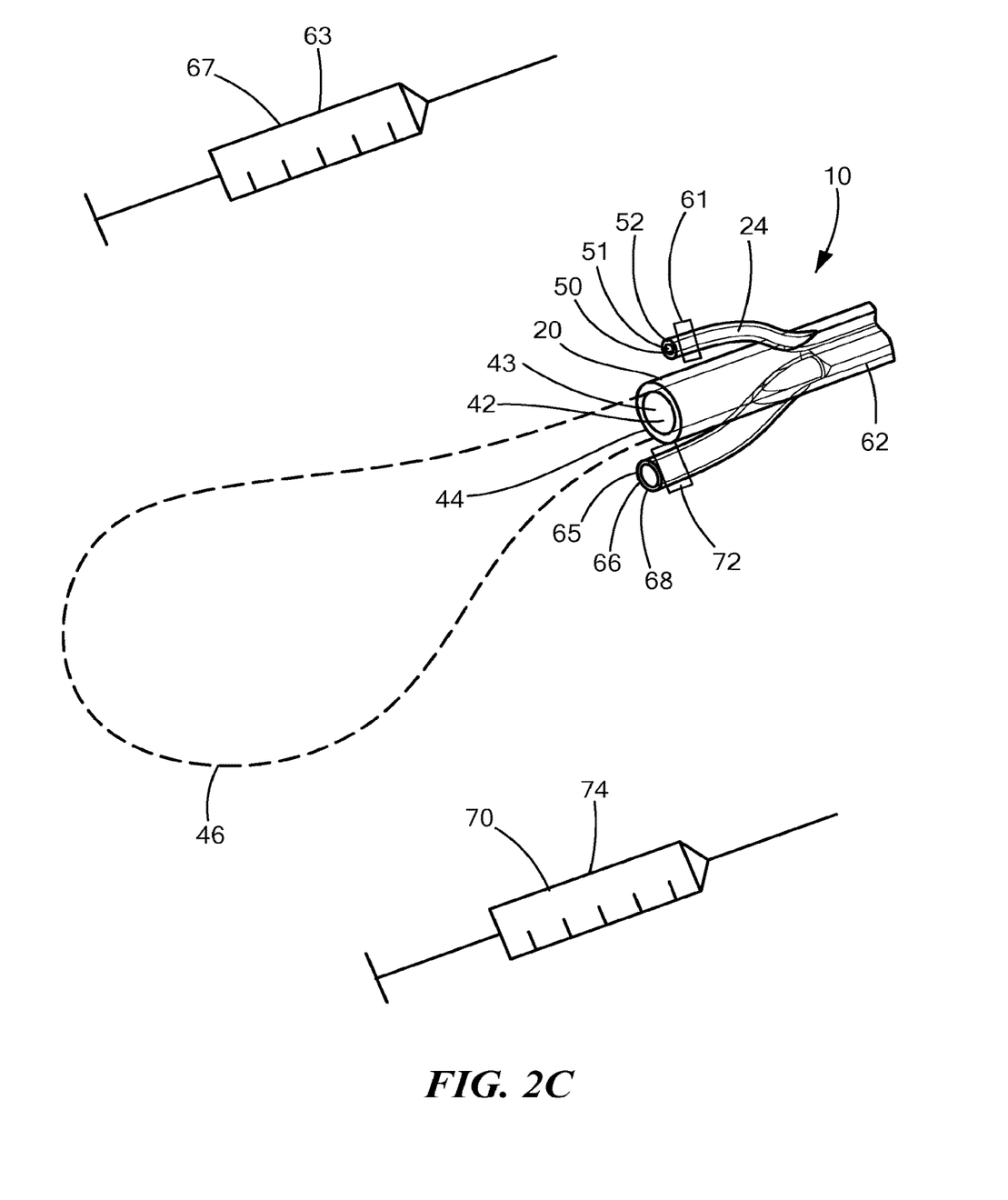
FIG. 2C is a sectional view according to one embodiment of the invention.

The first lumen (20) includes at least one drainage "eye" (38) or drainage inlet port disposed at the distal end (40) of the first lumen (20) and a drainage exit port (42) disposed at the proximal end (44) of the first lumen (20), as shown in FIGS. 2B and 2C. In a preferred embodiment, the first lumen is adapted to receive the first fluid from the drainage eye (38), to pass the first fluid along substantially the entire length of the first lumen (20), and to drain the first fluid from the first lumen (20) though the drainage exit port (42). The drainage exit port (42) can be adapted to attach to a bag (46) for the collection of the first fluid (22) including, for a non-limiting example, urine (23).

The at least one drainage "eye" (38) of the catheter (10) of the present invention can have a length in a range of 1.0 mm to 8.5 mm, and preferably in a range of 3.0 mm to 7.5 mm, and more preferably in a range of 6.0 mm to 6.5 mm; and a width in a range of 0.7 mm to 4.5 mm, and preferably in a range of 2.0 mm to 4.0 mm, and more preferably in a range of 3.0 to 3.5 mm. The dimensions of the drainage eye (38) are selected to facilitate and/or to optimize drainage.

Further, and in contrast to traditional indwelling catheters, in a preferred embodiment, the at least one drainage eye (38) of the novel improved catheter of the invention includes a smoothed outer edge (48). The smoothed outer edge (48) is adapted to minimize and/or prevent scraping, discomfort and/or trauma during insertion and removal of the catheter, and during bladder wall collapse and insertion of the catheter. In a preferred embodiment, the catheter of the invention includes more than one drainage eye (38), and in a more preferred embodiment, the catheter of the invention includes at least two drainage eyes (38) and (38'), each with a smoothed outer edge (48) and (48').

The second lumen (24) of the novel improved catheter (10) includes a second lumen inlet port (50) disposed at the proximal end (52) of the second lumen (24), and at least one second lumen outlet port (54) disposed at the distal end (56) of the second lumen, as shown in FIGS. 2B and 2C. In a preferred embodiment, the second lumen outlet port (54) includes an attachment port (58) adapted for attachment to the reversibly inflatable device (28). The second lumen outlet port (54) including the attachment port (58) can be configured for either reversible or irreversible attachment of the reversibly inflatable device (28), as necessary. In a preferred embodiment, the second lumen inlet port (50) includes an inflation/deflation port (51) adapted for connection to a second fluid injection/withdrawal device (63). The second lumen inlet port (50) including the inflation/deflation port (51) can include a second lumen connector (62) adapted for either reversible or irreversible connection to the second fluid injection/withdrawal device (63), such as, for a non-limiting example, a graduated syringe (67).

The second fluid injection/withdrawal device (63) can include one device which is adapted for both injection and withdrawal of a select amount of the second fluid (26). Alternatively, the second fluid injection/withdrawal device (63) can include separate second fluid injection and withdrawal devices, where the separate devices are respectively adapted for the injection and withdrawal of select amounts of the second fluid (26).

The second fluid (26) can include a sterile second fluid including a pure water, a saline, a synthetic urine equivalent, another fluid known to those of ordinary skill in the art for the inflation and/or deflation of a reversibly inflatable device (28), and a combination of at least two of the former fluids. For purposes of this application, the term a "synthetic urine equivalent" refers to a urine-like solution having bacteriostatic properties including for a non-limiting example, a urea component, and/or a pH substantially similar to natural urine. In different embodiments, the second fluid (26) includes a select amount of the second fluid (26) in a volumetric range of 5-30 mL per application or flush of the second fluid injection/withdrawal device (63).

In a preferred embodiment, the second lumen (24) is adapted to receive the second fluid (26) through the second lumen inlet port (50), to pass the second fluid (26) from the second lumen inlet port (50) along substantially the entire length of the second lumen (24) to the second lumen outlet port (54), and to pass the second fluid (26) through the second lumen outlet port (54) into the reversibly inflatable device (28), thereby inflating the reversibly inflatable device (28). Once inflated, the reversibly inflatable device (28) can stabilize the positioning of the catheter (10) within the distal catheter receiving region of the subject including, for non-limiting examples, an organ or other receptacle of the subject, such as the bladder. After a predetermined time period and/or after a select amount of the first fluid (22) is drained from the subject, the second lumen (24) can be adapted to receive the second fluid (26) from the reversibly inflatable device (28) through the second lumen outlet port (54), thereby deflating the reversibly inflatable device (28). The second lumen (24) can be further adapted to pass or re-pass the second fluid (26) from the second lumen's distal end (56) along substantially the entire length of the second lumen to the lumen's proximal end (52), and to drain the second fluid (26) from the second lumen (24) through the second lumen inlet port (50) into, optionally, the second lumen injection/withdrawal device (63).

The third lumen (30) includes a third lumen inlet port (65) disposed at the lumen's proximal end (68) and at least one third lumen outlet port (75) disposed at the lumen's distal end (34), as shown in FIGS. 2B and 2C. In a preferred embodiment, the third lumen inlet port (65) includes a flushing injection port (66) adapted for reversible or irreversible connection to a flushing injection device (70). In a preferred embodiment, the third lumen inlet port (65) includes a flushing injection device connector (72). In a preferred embodiment, the flushing injection device (70) includes a graduated syringe (74).

In a preferred embodiment, the third lumen (30) includes a primary lumen (62) including a first end contiguous with the third lumen inlet port (65) and a second end substantially opposed to the first end. The primary lumen (62) includes an interior passage which branches into and is interconnected to and in fluidic communication with at least one branch lumen (64) and preferably, at least two branch lumens (64) (64') disposed at the distal end (34) of the third lumen (30). The branch lumens (64) (64') can be configured in substantially opposing directions from one another. Each branch lumen (64) (64') has a first end contiguous with the second end of the primary lumen and a second end substantially opposed to the first end. In a preferred embodiment, the third lumen outlet port (75) is adapted as respective flushing ejection ports (76) (76') disposed at the respective second ends (78) (78') of the branch lumens (64) (64').

In a preferred embodiment, the third lumen (30) is adapted to receive a third fluid (32) through the third lumen inlet port (65) into the primary lumen (62) and to pass the third fluid (32) along substantially the entire length of primary lumen (62) into the at least one branch lumen (64)

and more preferably into the at least two branch lumens (64)(64') and through the third lumen outlet port (75) including respective flushing ejection ports (76) (76') whereupon the exiting third fluid (32) bathes at least a part of the outer surface (36) of the catheter. The branch lumen (64) or preferably, the branch lumens (64) (64') of the third lumen (30) allow for greater flush release, less random fluid flow and a more even distribution of fluid along the passage as compared to a singular branch or a primary lumen with no branches. The third fluid (32) cleans at least a portion of the outer surface of the catheter, and removes at least a portion of any bacterial film and/or encrustations which have developed between the outer surface of the catheter and the wall of the passage. The cleaning and removal of the biofilm reduces the risk of CAUTIs in patients during long term catheter use.

Figure 3A:
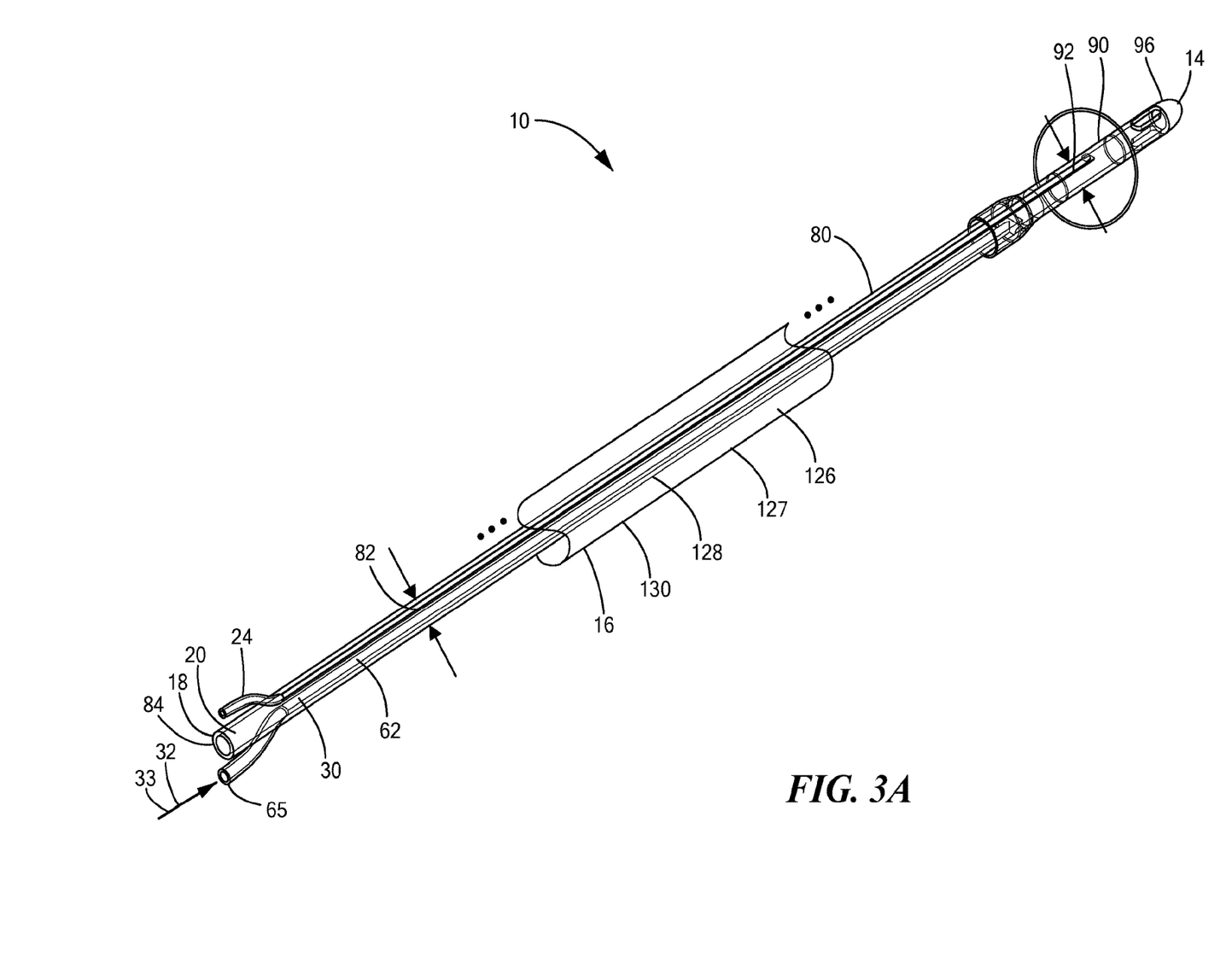
FIG. 3A is a sectional view according to one embodiment of the invention.
Figure 3B:
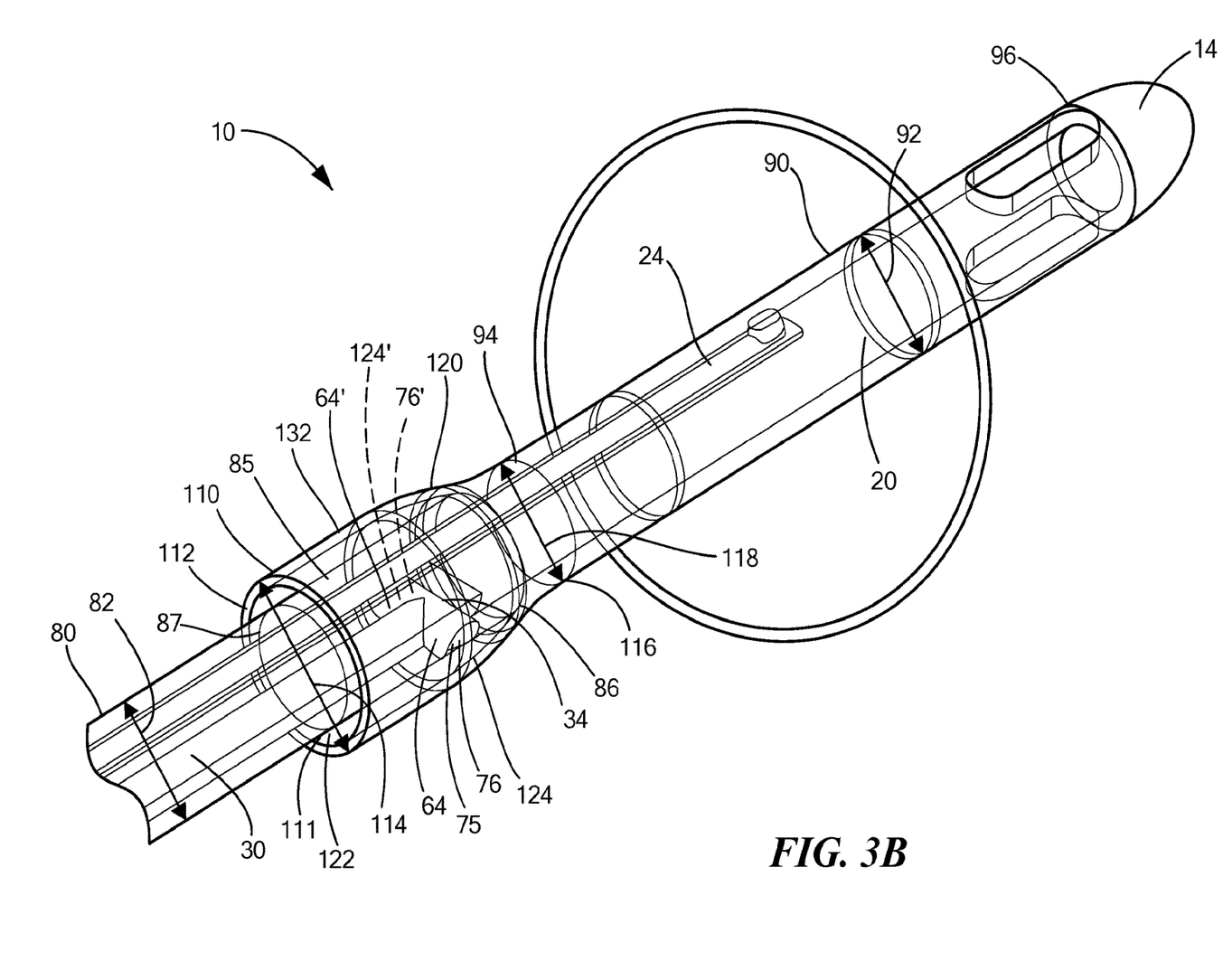
FIG. 3B is a sectional view according to one embodiment of the invention.

In a preferred embodiment, the novel improved catheter (10) further includes a lower portion (80) having a lower portion diameter (82) and a first end (84) contiguous with the proximal end (18) of the catheter (10), a second end (86) substantially opposed to the first end and disposed proximate to the distal end (34) of the third lumen (30), and an intermediate area (85) disposed between an intermediate circumference (87) and the second end (86) of the lower portion, as shown in FIGS. 3A-3B. The novel catheter (10) also includes an upper portion (90) having an upper portion diameter (92), a first end (94) disposed proximate to the distal end (34) of the third lumen (30) and a second end (96) contiguous with the closed insertable distal tip (14) of the catheter (10). In this preferred embodiment, the novel catheter further includes a bulb portion (110) which is disposed between the lower (80) and upper (90) portions. The bulb portion (110) overlaps the intermediate area (85) of the lower portion. At least part of the inner surface (111) of the bulb portion (110) forms an enclosure including a cavity (122) thereby acting like an umbrella over the overlapped intermediate area (85) of the lower portion (80). The bulb portion (110) has a first bulb end (112) which is disposed proximate to and surrounding the intermediate circumference (85) of the lower portion (80) and has a first bulb end diameter (114). The bulb portion (110) has a second bulb end (116) which is contiguous with the first end (94) of the upper portion (90) and has a second bulb end diameter (118). The diameter (114) of the first bulb end (112) is greater than the diameter (82) of the lower portion (80) of the catheter (10), and is also greater than the second bulb end diameter (118). The bulb portion (110) is constructed such that outer surface (120) of the bulb portion (110) gradually decreases in diameter from the first bulb end (112) to the second bulb end (116) to form a substantially smooth transition of decreasing diameter.

The first (20) and second (24) lumens can be configured to pass through the lower (80), bulb (110) and upper (90) portions of the catheter (10). The third lumen can be configured to pass through at least the lower and the bulb portion of the catheter. In a preferred embodiment, the third lumen passes through the lower portion and the bulb portion of the catheter, and more preferably, the branches (64) (64') of the third lumen are disposed within the internal cavity of the bulb portion, and most preferably, the volume of the internal cavity (122) of the bulb portion (110) is selected to accommodate a length, diameter and configuration of each of the branch lumens (64) (64'). The first bulb end diameter, the second bulb end diameter, and the diameter transition of the bulb portion (110) are selected to allow a gap (126) to be formed between at least part of the outer surface (128) of the lower portion (80) of the catheter and the wall (130) of the passage, such as, for a non-limiting example, the urethral wall. Thus, when the third fluid (32) including, for example, a flushing fluid (33) is injected via the flushing injection port (66) into the primary lumen (62), and the fluid passes through the primary lumen (62) into the branch lumens (64) (64') and through their respect flushing ejection ports (76) (76'), the fluid accumulates in the cavity (122) and ultimately is forced towards the proximal end of the catheter.

In a preferred embodiment, the second portion of the catheter has a length selected to maintain non-interference of the bulb portion with the workings of a tissue or an organ of the subject such as, for a non-limiting example, the bladder of the subject.

In alternative embodiments, the bulb portion (110) includes one or more bulb delivery ports (124) (124') either contiguous or non-contiguous with the at least two flushing ejection ports (76) (76') of the branch lumens. The bulb delivery ports (124) (124'), the flushing ejection ports (76) (76'), or both the bulb delivery ports (124) (124') and the flushing ejection ports (76) (76') can be angled towards the proximal end (18) of the catheter (10) to promote flow of the third fluid (30) including a flushing or irrigation fluid into a lower section of the passage (16), such as, for a non-limiting example, the urethra, and towards a proximal end of the catheter.

In another embodiment, the bulb portion includes an expandable material (132). Upon injection of the third fluid (32) into the third lumen inlet port (65), the fluid (32) passes through the third lumen (30) and exits via third lumen outlet port (75) into the cavity (122) of the bulb portion (110). In a preferred embodiment, upon injection of the third fluid (32) into the third lumen inlet port (65), the fluid passes through the third lumen (30) including a primary lumen (62). The fluid (32) then passes through at least one branch lumen (64) and more preferably through at least two branch lumens (64) (64'). The fluid (32) exits through the third lumen outlet port (75) including preferably at least one flushing ejection port (76) and more preferably including at least two flushing ejection ports (76) (76') of the at least two branch lumens (64) (64'). The emptying of the fluid (32) or (33) into the cavity (122) causes the cavity (122) to expand thereby forming an expanded gap (126) between the outer surface of at least a part of the lower portion of the catheter and the wall of the passage such as, for a non-limiting example, the urethra. The fluid then bathes at least a part of the lower portion (80) of the catheter (10). The expanded gap (126) allows the fluid to accumulate in the expanded gap (126) and to flow towards a proximal end (84) of the lower portion (80) of the catheter (10). After all the fluid exits the catheter (10), the expandable bulb portion (132) is adapted to deflate in response to drainage of the third fluid (32) including the flushing fluid (33) and pressure of the wall of the passage. In one embodiment, the flushing injection device (70) can be attached or reattached, as necessary, to the flushing injection port (66) and used to deflate the expandable material (132) of the bulb portion (110).

In a preferred embodiment, the dimensions of the third lumen outlet port (75) and in a more preferred embodiment, the dimensions of the third lumen outlet port (75) including the flushing injection ports (76) (76') of the branch lumens (64) (64') are selected to maintain a rate of flow of the third fluid exiting the third lumen which is less than the rate of flow of injection of the third fluid into the third lumen inlet port such that the bulb portion (110) maintains fluid within the internal cavity (122) of the bulb portion (110) for a pre-determined time period. In another preferred embodiment, the dimensions of the third lumen outlet port and in a more preferred embodiment, the dimensions of the third lumen outlet port (75) including the flushing injection ports (76) (76') of the branch lumens (64) (64') are selected to ensure a pre-determined fluid flow velocity.

In different embodiments, at least one of the first, second and third lumens of the novel improved catheter has a circular cross section. In other embodiments, at least one of the first, second and third lumens of the novel improved catheter has a non-circular cross section. In a preferred embodiment, the first, second and third lumens of the novel, improved catheter have circular cross sections. In one embodiment, the first lumen has a non-circular cross section adapted to accommodate the cross sections of the second lumen and the third lumen disposed between an exterior surface of a wall of the first lumen and an interior surface of an outer wall of the catheter.

In different embodiments, the branches of the third lumen are disposed at an angle between 0 and 180 degrees from one another. In different embodiments, at least one of the branches is disposed obliquely, substantially parallel, or orthogonally to the primary lumen. In a preferred embodiment, the third lumen branches are disposed such that the third lumen outlet port including at least one of the flushing ejection ports is disposed at an angle facing substantially towards the proximal end of the catheter, whereby the bathing of the outer surface of at least a part of the catheter by the fluid exiting from the third lumen is optimized. In yet another embodiment, the third lumen branches are disposed within at least one of the lower, the bulb and the upper portions of the catheter. In one embodiment, the third lumen branches are disposed in the upper and bulb portions of the catheter.

In other embodiments, the branches of the third lumen are disposed in the bulb portion and the lower portion, in the bulb portion and the upper portion, or in the bulb portion, the lower portion and the upper portion.

Figure 4A:
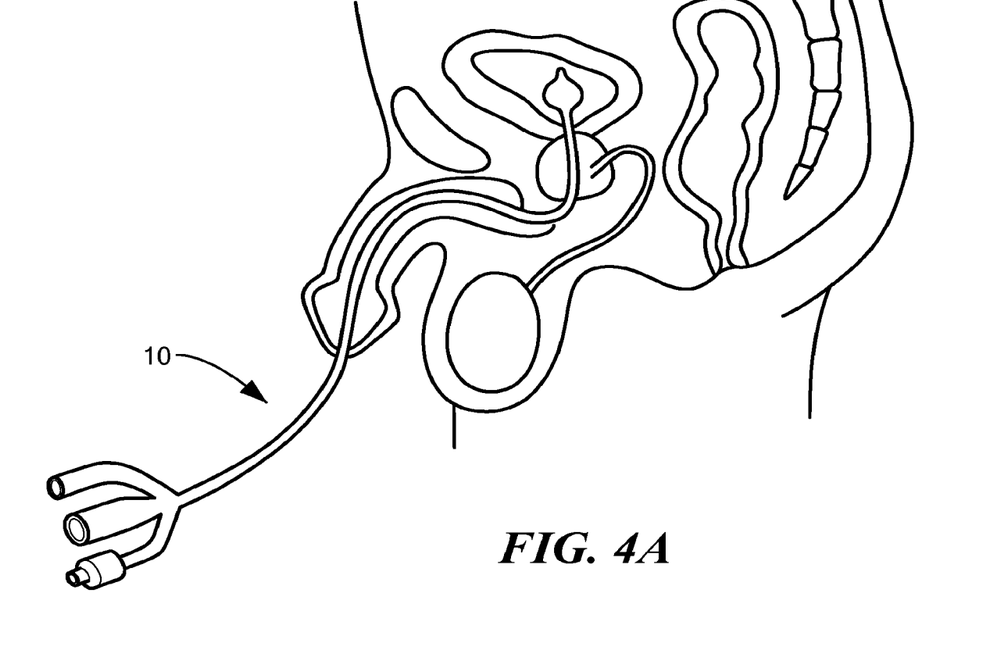
FIG. 4A is a sectional view according to one embodiment the invention.
Figure 4B:
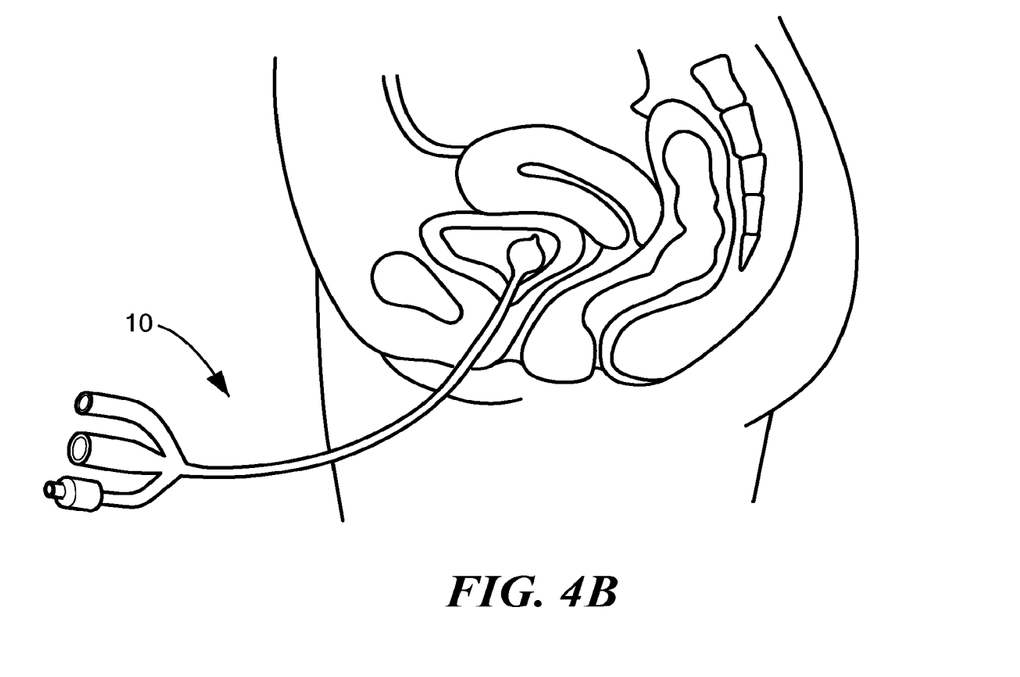
FIG. 4B is a sectional view according to one embodiment the invention.

The present invention can be used in the urinary tracts of male and female patients, as shown in FIG. 4A and FIG. 4B, respectively. In different embodiments, the closed insertable distal tip or end of the catheter can be adapted, as needed, to facilitate insertion and/or stabilization upon insertion. The closed insertable distal tip or end of the catheter can include: (a) a straight tip; or a (b) Coude tip.

In one embodiment, the invention provides the tri-lumen catheter having at least one groove on at least a part of an outer surface of the catheter. The groove is adapted for directing the flow of the flushing fluid on at least a part of the outer surface of the catheter for a more even distribution of the flushing fluid and hence an improved cleaning of the outer surface of the catheter. The groove can be configured as one or more straight and/or parallel grooves, as one or more non-straight grooves, and/or as one or more spiral grooves. In a preferred embodiment, the edges of the groove or grooves are smoothed to avoid the urethral membrane catching on the groove edges thereby causing discomfort or trauma during insertion or removal of the catheter. Additional or other surface features may be provided to serve the same function in alternative embodiments. In one embodiment, the tri-lumen catheter of the invention, including for a non-limiting example, the grooved tri-lumen catheter, can include a drainage exit port, an inflation/deflation port, and a flushing injection port. In another embodiment, the tri-lumen catheter of the invention, including for a non-limiting example, the grooved tri-lumen catheter, can include a turn valve, in lieu of separate inflation fluid injection and flushing injection ports. The turn valve can be adapted for injection of an inflation fluid or deflation when the turn valve is set or turned to one position, and further adapted for injection of a flushing fluid when the turn valve is set or turned to a second position.

The third fluid including the flushing fluid can include saline. Medical grade saline is sterilized, biocompatible, and is a current industry standard fluid and is used for many in-vivo applications (including wound cleansing and intravenous fluid replacement). Alternatively, the third fluid can include a sterile third fluid including a pure water, a saline, a synthetic urine equivalent, another fluid known to those of ordinary skill in the art for the flushing of an outer surface of a catheter, and a combination of at least two of the former fluids.

In yet another embodiment, the second and the third fluids have substantially the same composition or can have the same source. In a further embodiment, the same device can serve as the inflation/withdrawal device and the flushing device. In still a further embodiment, at least one of the second and the third fluids includes natural urine.

In other embodiments, at least one of the second and third fluids can include at least one of an analgesic agent adapted for pain reduction in the subject; a paralytic agent adapted for the reduction of a tissue spasm, such as, for a non-limiting example, a bladder spasm, in the subject; a chemotherapy agent adapted for the therapeutic treatment of a tumor and/or enhancement of a tumor therapy in the subject; an antibiotic agent and/or a prophylactic antibiotic agent adapted for the prevention, treatment, and/or reduction of infection in the subject; an intra-vesical treatment agent adapted for the prevention, treatment and/or reduction of painful bladder syndrome or interstitial cystitis in the subject; and a medicinal agent adapted for the treatment of the urinary tract and/or the appellate tissues and organs surrounding the urinary tract, wherein the medicinal agent can have a treatment effect in the subject within and in some embodiments, additionally beyond the urinary tract and/or appellate tissues and organs surrounding the urinary tract.

The invention also features a kit and/or system including the novel improved catheter including the catheter balloon and other elements necessary for use with the catheter such as, for non-limiting examples, an inflation fluid injection device, an inflation fluid, a flushing fluid injection device, a flushing fluid, and other elements known to those of ordinary skill in the art for use with catheter for either short term or long term indwelling catheter use.

The overall dimensions of the catheter and the dimensions of the first, second and third lumens can be designed to optimize the drainage, inflation, and flushing requirements of the respective catheter, as necessary, according to the knowledge of one of ordinary skill in the art. The catheter of the invention can be sized or scaled in a range from a 5 French catheter to a 26 French catheter, and preferably in a range from a 10 French catheter to a 24 French catheter and more preferably in a range from a 16 French catheter to a 22 French catheter, and most preferably to a 20 French catheter. The first lumen can have a diameter in a range of 0.6 mm to 5.0 mm. The second lumen can have a diameter in a range of 0.1 mm to 1.7 mm. The third lumen can have a diameter in a range of 0.5 mm to 7.0 mm.

In an alternative aspect of the invention, the novel improved catheter can include a first lumen and a third lumen, as described above, without the second lumen. In embodiments of this aspect of the invention, the novel improved catheter can include one or more of the features described above with respect to the first and third lumens.

The invention also features a method of use of the novel, improved catheter of the invention. The method generally includes inserting the tri-lumen catheter of the invention into a subject; passing a second fluid through a second lumen and inflating a reversibly inflatable device in fluidic communication with the second lumen; passing a third fluid through a third lumen and flushing at least a part of an outer surface of the catheter with the third fluid; and draining the first fluid from the subject via the first lumen. The method also can generally further include passing, withdrawing or re-passing the second fluid through the second lumen thereby deflating the reversibly inflatable device; and withdrawing the catheter from the subject.

Figure 5:
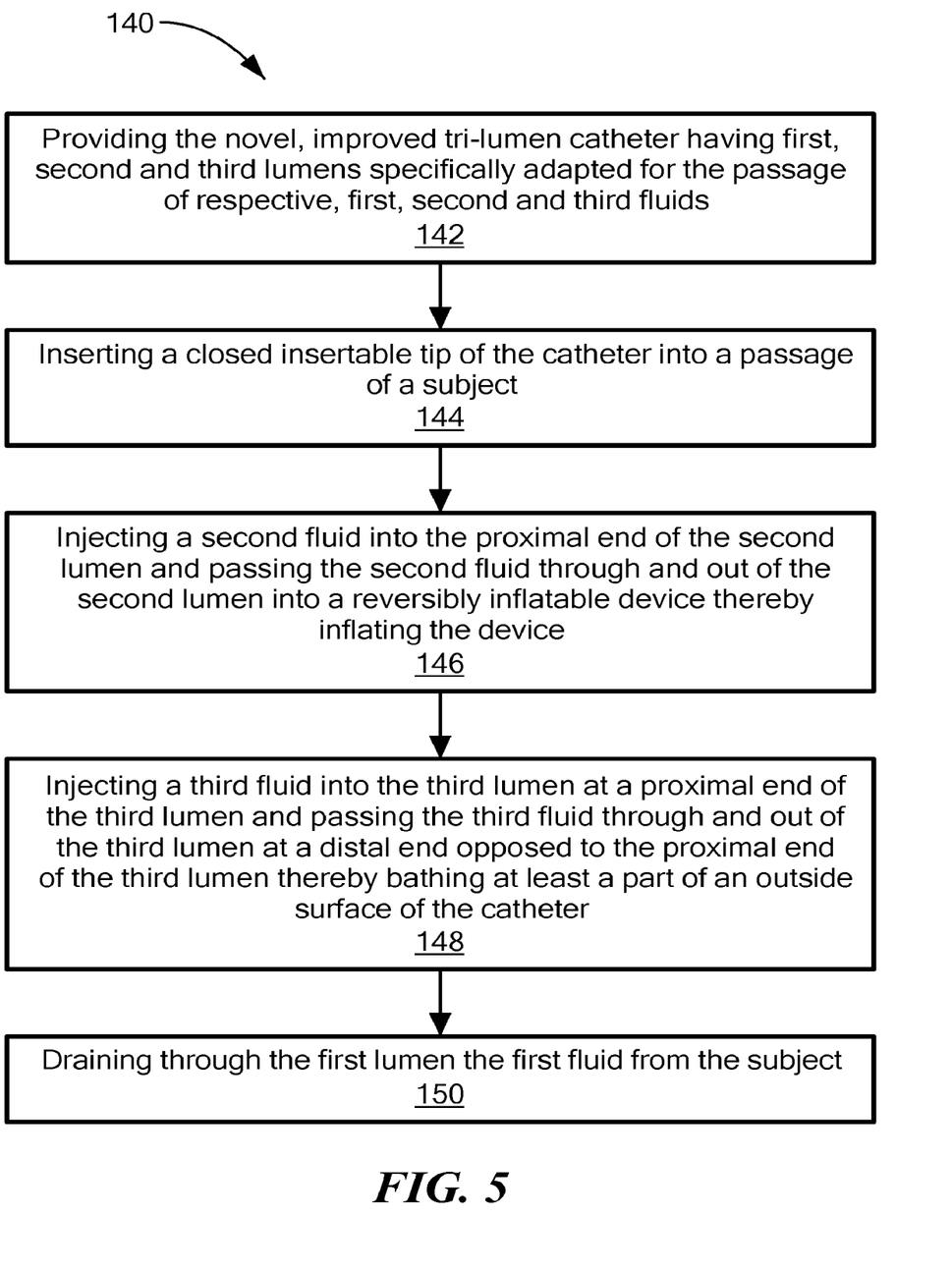
FIG. 5 is a flow chart of a method according to an embodiment of the present invention.

In one aspect, the method (140) of the invention features providing the novel and improved tri-lumen catheter (step 142), where the first, second and third lumens are adapted respectively for passing a first fluid through the first lumen, passing a second fluid through the second lumen, and passing a third fluid through the third lumen, as illustrated in FIG. 5. The method includes inserting a closed insertable tip of the catheter into a passage (step 144), such as, for a non-limiting example, a urethra, of a subject. The method also includes injecting the second fluid into the proximal end of the second lumen and passing the fluid through and out of the second lumen at the distal end substantially opposed to the proximal end of the second lumen into a reversibly inflatable device, such as, for a non-limiting example, a catheter balloon, and inflating the device (step 146). The method also includes injecting the third fluid into a proximal end of the third lumen, passing the third fluid through and out of the third lumen at a distal end substantially opposed to the proximal end of the third lumen, and bathing at least a part of the outer surface of the catheter (step 148). In addition, the method also includes draining the first fluid from the subject through the first lumen (step 150). The steps of the method are illustrated in FIG. 5.

In another embodiment, the method includes the providing, inserting, injecting the second fluid, and draining the first fluid steps above. In addition, the method includes injecting the third fluid into the third lumen at a proximal end of the third lumen and passing the third fluid through and out of the third lumen at a distal end substantially opposed to the proximal end of the third lumen; accumulating the third fluid in a cavity formed by a umbrella shaped bulb portion of the catheter; and bathing at least a part of the outer surface of the catheter with the third fluid.

In different embodiments, the providing step includes providing the novel improved catheter including the various features previously described in this application.

In another embodiment, the method includes withdrawing the second fluid from the reversibly inflatable device thereby substantially deflating the reversibly inflatable device and withdrawing, passing or re-passing the second fluid through substantially the entire length of the second lumen. In still another embodiment, the method includes removing the catheter from the subject.

Comparative testing of standard and modified catheters showing the flushing mechanism of the invention is provided in the following Example.

EXAMPLE

Method: The controlled experiment was conducted using a standard *Escherichia Coli* K12 strain as the bacterial inoculation broth. This genus family is one of the most common causative bacterium of urinary tract infection. The same broth was used across all experiments. Sterile cotton swabs were streaked onto standard LB agar plates using preset points of contact in order to ensure similarity across all plates.

A standard 16 French Bard Foley catheter was used as the prior art standard test catheter (hereinafter the standard test catheter).

A 16 French Bard Foley catheter was modified in order to simulate the novel catheter of the invention (hereinafter the modified test catheter). In the modified test catheter, the lower half of the catheter balloon was removed from the 16 French Bard Foley catheters while leaving the upper half of the catheter balloon intact. Flushing saline injected into the modified test catheter flowed upwards through the catheter lumen and when meeting resistance at the remaining balloon portion, the flushing saline was forced to flow outside the modified catheter along its exterior surface. This effect created the flushing mechanism.

A standard dummy rubber urethra was used to simulate a patient urethra. The dummy urethra included an opening sized to accommodate each 16 French catheter with no more than 3 mm of clearance around catheter. Accordingly, each test catheter fit snugly inside the dummy urethra and realistically simulated catheter insertion into a patient urethra. The work surface, the dummy urethra including the rim of the rubberized urethra opening, the exterior surfaces and interior lumens of the test catheters, and the metal plating devices were sterilized using ethanol. A Bunsen burner was used to further sterilize the metal plating devices.

Pre-sterilized saline, agar plates, 30 ml sterile syringes and cotton swabs were provided for the experiment.

Further, the syringes and the exterior surface and interior lumen of each test catheter were sterilized after each use with an additional washing with ethanol.

A saline moistened sterile cotton swab was used to swipe the dummy urethra and applied to one of the pre-set Agar plates to create a control group for confirming urethra sterilization.

Pre-inoculation: A sterile cotton swab was first dipped into a tube of sterile saline to absorb 0.2 ml of saline into the tip for subsequent better bacterial adherence to the cotton swab tip. The swab was then applied to the exterior surface of a standard test catheter for a preset distance marked with permanent marker while rotating the swab. The swab was then applied to an agar plate hitting 10 points, pre-marked on the plates for complete "Z" style coverage to create a control group for confirming sterilization of the standard test catheter.

Inoculation: A sterile cotton swab was dipped into the *E. coli* broth to absorb approximately 0.2 ml of bacterial broth and applied to the exterior surface of the standard catheter as described above for the pre-inoculation procedure. The standard test catheter was inserted into the dummy urethra until it encountered the end wall of the dummy urethra, approximately 7 inches from the opening of the urethra. After 60 seconds, the standard test catheter was removed with sterile gloves.

Post inoculation: A new sterile cotton swab moistened with 0.2 ml of sterile saline to maximize bacterial adherence was applied to the exterior surface of the standard test catheter for the preset distance while rotating the swab and the swab was then applied to an agar plate hitting 10 points, pre-marked on the plate for complete "Z" style coverage.

The pre-inoculation and inoculation procedures were repeated with a modified test catheter. After waiting 60 seconds, a flush of 30 mL sterile saline was injected into the modified test catheter by attaching a 30 mL syringe to the inflation/deflation port and an injecting the flushing saline fluid. The fluid met resistance at the remaining balloon portion and exited the modified test catheter to bathe its exterior surface. Then the modified test catheter was removed from the dummy urethra with sterile gloves. The modified test catheter was then re-swabbed followed by plating using the post-inoculation procedure.

The agar plates were left in a 37° C. incubator for 24 hours after which a clear filter with gridlines creating 172 rectangles was used to analyze the agar plates for bacterial colonies. Any rectangle that demonstrated any growth within the perimeter was counted as a "bacterial colony unit".

The above tests were repeated 3 times using the standard test catheter and using two different modified test catheters. All equipment and the dummy urethra were sterilized between tests.

Figure 6:
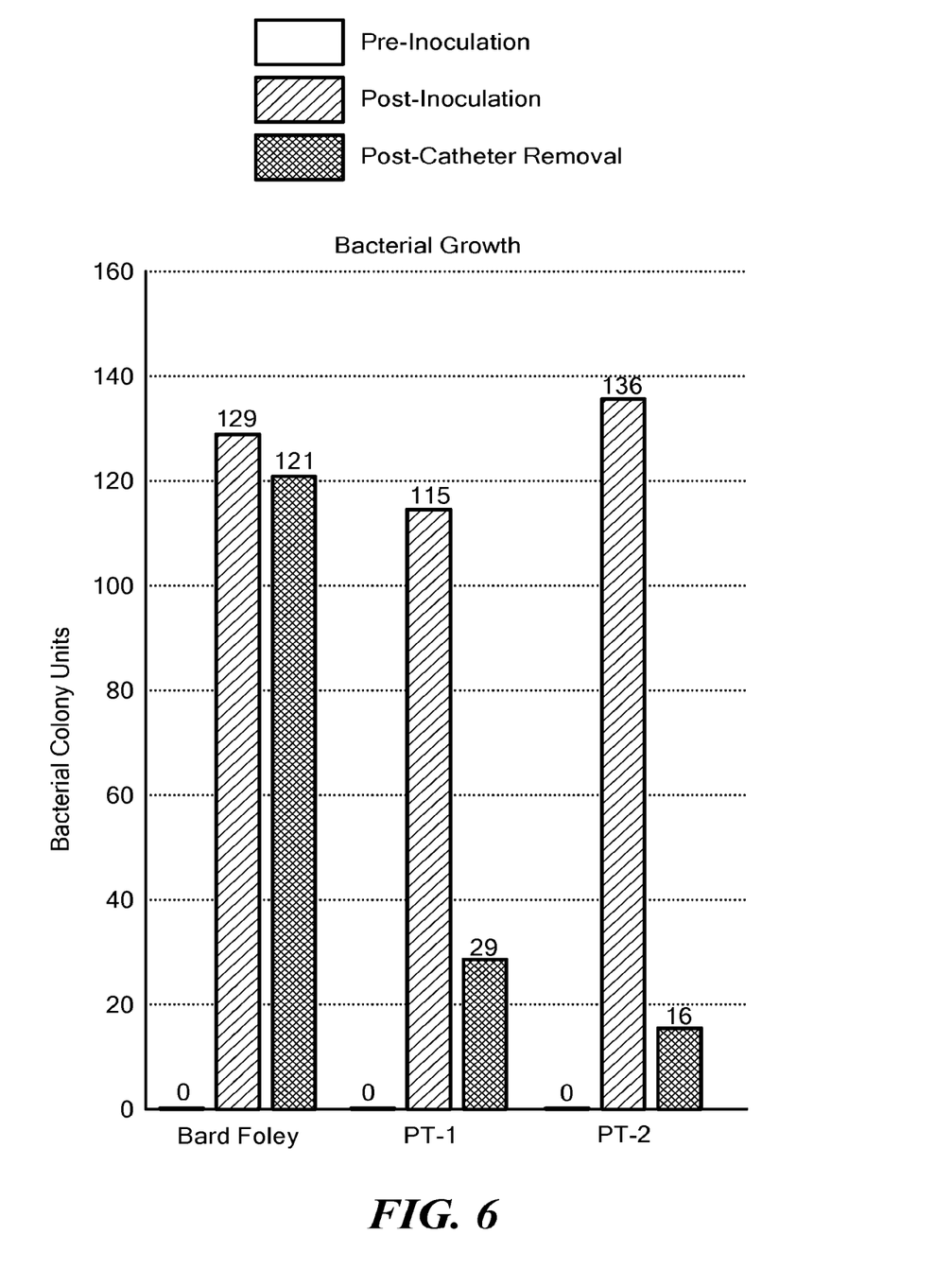
FIG. 6 shows experimental results achieved with one embodiment the invention.

Results: As seen in FIG. 6, both prototype trials (PT-1 and PT-2) displayed significant reduction in bacterial colony units compared to the control Bard Foley catheter. The pre-inoculation results across all three trials show no bacterial growth confirming that the catheters were sterile prior to inoculation. The control Foley catheter showed a 6.2% reduction in bacterial growth from post-inoculation to post-catheter removal. The PT-1 trial showed a 74.8% reduction in bacterial colony growth and the PT-2 trial showed 88.2% reduction. Thus, the two prototype tests averaged a reduction in bacterial colony growth of 81.5%. Assuming a standard error of 6.2% from the control group, it can be concluded that the overall bacterial growth reduction from a single saline flush is 75.3%.

The foregoing examples and detailed description are not to be deemed limiting of the invention which is defined by the following claims. The invention is understood to encompass such obvious modifications thereof as would be apparent to those of ordinary skill in the art.

What is claimed is:

1. A method for flushing a passage of a subject comprising:
   providing a catheter comprising:
      a first lumen adapted for passing a first fluid through at least a portion of the catheter,
      a second lumen adapted for passing a second fluid through at least a portion of the catheter, and
      a third lumen adapted for passing a third fluid through at least a portion of the catheter, the third lumen having a third lumen outlet port configured to allow the third fluid to exit the third lumen, and
      a bulb extending axially along at least a portion of a length of the catheter toward a proximal end of the catheter, at least a portion of the bulb extending from an outer surface of the catheter and being radially outward of the third lumen outlet port after introducing the third fluid into the third lumen;
   inserting a closed insertable tip of the catheter into the passage of the subject; and
   injecting the third fluid into the third lumen at a proximal end of the third lumen, and passing the third fluid through the third lumen and out of the third lumen outlet port, the bulb redirecting the third fluid exiting through the third lumen outlet port toward the proximal end of the catheter at a velocity capable of removing at least a portion of a biofilm, bacterial film, and/or encrustations between an outside surface of the catheter and a wall of the passage of the subject.

2. The method of claim 1, wherein the catheter includes at least one drainage eye at a distal end of the first lumen.

3. The method of claim 2, wherein the at least one drainage eye has a smooth outer edge.

4. The method of claim 1, wherein the catheter further includes:
   a lower portion having a lower portion diameter, a first end contiguous with a proximal end of the catheter, a second end substantially opposed to the first end, and an intermediate area extending from an intermediate circumference of the lower portion to the second end of the lower portion; and
   an upper portion having an upper portion diameter, a first end, and a second end substantially opposed to the first end and contiguous with the closed insertable tip of the catheter,
   wherein the bulb has a first bulb end having a first bulb end diameter, a second bulb end substantially opposed to the first bulb end and having a second bulb end diameter, the second bulb end being contiguous with the first end of the upper portion, the first bulb end diameter being greater that the lower portion diameter and being greater than the second bulb end diameter, the first bulb end being disposed proximate to and surrounding the intermediate circumference of the lower portion, and at least part of an inner surface of the bulb portion forming an enclosure including a cavity surrounding an outer surface of the intermediate area of the lower portion.

5. The method of claim 4, wherein the lower portion diameter and the first bulb end diameter are selected to form a predetermined gap between at least a part of an outer surface of the catheter and the wall of the passage of the subject upon insertion of the catheter into the subject.

6. The method of claim 1, wherein the bulb is disposed at a predetermined distance from the closed insertable tip of the catheter to minimize disruption of a tissue of the subject upon insertion of the catheter into the subject.

7. The method of claim 1, wherein the catheter is a substantially straight tube.

8. The method of claim 1, wherein the third lumen comprises:
   a primary lumen having a first end contiguous with a proximal end of the catheter and a second end substantially opposed to the first end, and
   at least two branch lumens each having a first end contiguous with the second end of the primary lumen and each having a second end substantially opposed to the first end, each branch lumen in fluidic communication with the primary lumen and branching out in a direction substantially opposed to the other branch lumen.

9. The method of claim 1, wherein the first, the second and/or the third lumen has a circular cross-section.

10. The method of claim 1, wherein the outer surface of the catheter is selected from the group consisting of a smooth outer surface and a grooved outer surface.

11. The method of claim 1, further comprising:
   injecting the second fluid into a proximal end of the second lumen, and passing the second fluid through and out of the second lumen at a distal end substantially opposed to the proximal end of the second lumen into a reversibly inflatable device, thereby inflating the device.

12. The method of claim 11 further comprising:
   withdrawing the second fluid from the reversibly inflatable device thereby deflating the reversibly inflatable device; and
   removing the catheter from the subject.

13. The method of claim 11, wherein the second lumen comprises an attachment port disposed proximate to a distal end of the second lumen and configured for attachment to the reversibly inflatable device.

14. The method according to claim 1, further comprising draining, through the first lumen, the first fluid from the subject.

15. The method according to claim 1, wherein the bulb is configured to redirect the third fluid exiting through the third lumen outlet port such that the third fluid flows substantially parallel to the outer surface of the catheter and toward the proximal end of the catheter.

16. The method according to claim 1, wherein the portion of the bulb radially outward of the third lumen outlet port is configured to be located between the third lumen outlet port and the wall of the passage of the subject, thereby redirecting the third fluid exiting the third lumen outlet port prior to the third fluid contacting the wall of the passage of the subject when the catheter is inserted in the subject.

17. The method according to claim 1, wherein the catheter is a urinary catheter.

18. The method according to claim 1, wherein the passage of the subject is a urinary tract of the subject.

* * * * *